US012570688B2

(12) United States Patent
Liu

(10) Patent No.: US 12,570,688 B2
(45) Date of Patent: Mar. 10, 2026

(54) ACTIVATED CYSTEINE-DIRECTED POLYPEPTIDE LIGATION TECHNIQUE

(71) Applicant: The Texas A&M University System, College Station, TX (US)

(72) Inventor: Wenshe Liu, College Station, TX (US)

(73) Assignee: The Texas A&M University System, College Station, TX (US)

( * ) Notice: Subject to any disclaimer, the term of this patent is extended or adjusted under 35 U.S.C. 154(b) by 787 days.

(21) Appl. No.: 17/783,639

(22) PCT Filed: Jan. 3, 2020

(86) PCT No.: PCT/US2020/012128
§ 371 (c)(1),
(2) Date: Jun. 8, 2022

(87) PCT Pub. No.: WO2021/137870
PCT Pub. Date: Jul. 8, 2021

(65) Prior Publication Data
US 2023/0002442 A1 Jan. 5, 2023

(51) Int. Cl.
*C07K 1/10* (2006.01)
*C07K 1/107* (2006.01)

(52) U.S. Cl.
CPC .............. *C07K 1/1077* (2013.01); *C07K 1/10* (2013.01)

(58) Field of Classification Search
CPC .................................................. C07K 1/1077
See application file for complete search history.

(56) References Cited

U.S. PATENT DOCUMENTS

| | | |
|---|---|---|
| 6,103,882 A | 8/2000 | Masato et al. |
| 2010/0322958 A1 | 12/2010 | Bardotti et al. |
| 2011/0124011 A1 | 5/2011 | Niedenthal et al. |
| 2013/0078671 A1 | 3/2013 | Liu |

FOREIGN PATENT DOCUMENTS

| | | |
|---|---|---|
| WO | WO-2003/099852 A2 | 12/2003 |
| WO | WO-2008/038296 A2 | 4/2008 |
| WO | WO-2013/148727 A1 | 10/2013 |
| WO | WO-2014/012181 A1 | 1/2014 |

*Primary Examiner* — Suzanne M Noakes
(74) *Attorney, Agent, or Firm* — Jackson Walker LLP

(57) ABSTRACT

Embodiments of the present disclosure pertain to methods of conjugating a molecule to a polypeptide by (1) modifying one or more thiol residues on the polypeptide, where the modifying includes cyanylation of the one or more thiol residues; and (2) associating the polypeptide with the molecule, where the associating results in the conjugation of the molecule to the polypeptide through a reaction between a nucleophilic moiety on the molecule and the one or more modified thiol residues. The cyanylation may include attachment of cyano groups to sulfur atoms of the one or more thiol residues to form thiocyanato groups that undergo reversible intramolecular addition with a nearby N-amide group to generate a 1-acyl-2-iminothiazolidine intermediate. Thereafter, the nucleophilic moiety on the molecule reacts with the 1-acyl-2-iminothiazolidine intermediate to replace 2-iminothiazolidine in a nucleophilic acyl substitution reaction and result in the conjugation of the molecule to the polypeptide.

19 Claims, 7 Drawing Sheets
Specification includes a Sequence Listing.

NEDD8-P: FLAG-NEDD8-G76Pa        SUMO3'-P: FLAG-SUMO3'-G92Pa
SUMO1'-P: FLAG-SUMO1'-G97Pa      SUMO4'-P: FLAG-SUMO4'-G93Pa
SUMO2'-P: FLAG-SUMO2'-G93Pa      ISG15'-P: FLAG-ISG15'-G157Pa
                                  GABARAPL2-P: FLAG-GABARAPL2-G116Pa

ACTIVATED CYSTEINE-DIRECTED POLYPEPTIDE LIGATION TECHNIQUE

STATEMENT REGARDING FEDERALLY SPONSORED RESEARCH

This invention was made with government support under Grant No. R01GM127575 awarded by National Institutes of Health, and Grant No. R01GM121584 awarded by the National Institutes of Health. The government has certain rights in the invention.

INCORPORATION BY REFERENCE STATEMENT OF THE MATERIAL CONTAINED IN THE "SEQUENCE LISTING" FILE

The Sequence Listing ASCII file submitted herewith is identified as follows:
Date of Creation: Sep. 19, 2025; Sequence File Name: 130466.00214_Sequence_ST25; Size in bytes: 870 bytes.

BACKGROUND

Current methods of conjugating proteins to various molecules suffer from numerous limitations, such as inconsistent results with different proteins, stringent reaction conditions, and inability to effectively target C-terminal residues of proteins. Various embodiments of the present disclosure address the aforementioned limitations.

The development of this invention was funded in part by the Welch Foundation under grant number A-1715.

SUMMARY

In some embodiments, the present disclosure pertains to methods of conjugating a molecule to a polypeptide. In some embodiments, the methods of the present disclosure occur through the following steps: (1) modifying one or more thiol residues on the polypeptide, where the modifying includes cyanylation of the one or more thiol residues; and (2) associating the polypeptide with the molecule, where the associating results in the conjugation of the molecule to the polypeptide through a reaction between a nucleophilic moiety on the molecule and the one or more modified thiol residues.

In some embodiments, the cyanylation includes attachment of cyano groups to sulfur atoms of the one or more thiol residues to form a thiocyanato group. In some embodiments, the thiocyanato group undergoes reversible intramolecular addition with a nearby N-amide to generate a 1-acyl-2-iminothiazolidine intermediate. Thereafter, the nucleophilic moiety on the molecule reacts with the 1-acyl-2-iminothiazolidine intermediate to replace 2-iminothiazolidine in a nucleophilic acyl substitution reaction and result in the conjugation of the molecule to the polypeptide.

In some embodiments, the polypeptide includes a peptide. In some embodiments, the polypeptide includes a protein, such as a recombinant protein. In some embodiments, the polypeptide includes, without limitation, ubiquitin (Ub), ubiquitin-like proteins (Ubls), and combinations thereof. In some embodiments, the Ub and Ubl proteins include, without limitation, SUMO1, SUMO2, SUMO3, SUMO4, ISG15, FAT10, MNSF beta, UFM1, ATG12, URM1, HUB1, GABARAP, GABARAPL2, and combinations thereof.

In some embodiments, the one or more thiol residues on the polypeptide are near the C-terminus of the polypeptide.

In some embodiments, the one or more thiol residues on the polypeptide are near the C-terminus of the polypeptide but not the last amino acid at the C-terminus.

In some embodiments, the molecule includes, without limitation, small molecules, macromolecules, lipids, oligonucleotides, peptides, polypeptides, proteins, polyethylene glycols, fluorophores, chromophores, and combinations thereof. In some embodiments, the molecule includes a peptide, such as a therapeutic peptide. In some embodiments, the nucleophilic moiety of the molecule is an amine group. In some embodiments, the amine group includes, without limitation, primary amines, secondary amines, hydrazine, hydrazides, hydroxylamines, O-alkylhydroxylamines, ammonia, and combinations thereof.

DESCRIPTION OF THE DRAWINGS

FIG. 2 illustrates protein synthesis methods through ligation.

FIG. 3 illustrates the synthesis of ubiquitin (Ub) conjugates by activated cysteine-directed protein ligation.

FIG. 4 illustrates the synthesis of Pa- and AMC-conjugated Ub and Ubl proteins by activated cysteine-directed protein ligation and their applications in the detection of Ub and Ubl protease activities.

FIG. 5 shows the synthesis of H2AK129ac and RNase H by activated cysteine-directed protein ligation.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

The advent of native chemical ligation and its related techniques has revolutionized the protein and peptide chemistry field. Groundbreaking applications include the synthesis of a large variety of proteins such as histones, kinases, and RAS proteins with posttranslational modifications for driving basic research advances and the production of many proteins or enzymes for therapeutic and biotechnological purposes.

Figures 1, 2A:
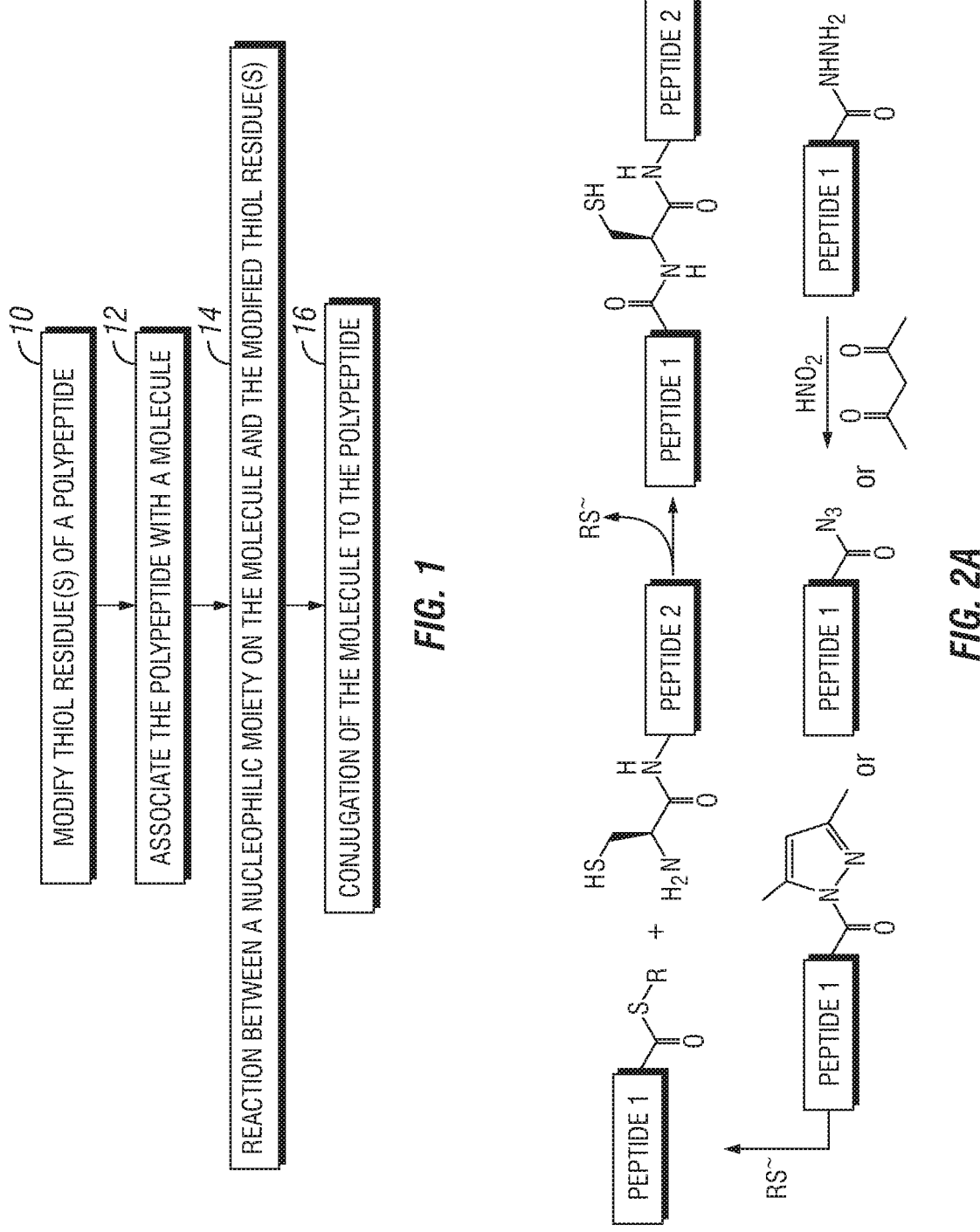
FIG. 1 illustrates a method of conjugating a molecule to a polypeptide.
FIG. 2A illustrates a native chemical ligation technique and a derivative technique entitled peptide hydrazide ligation.

For instance, proteins with a functionalized C-terminus are key to the synthesis of larger proteins by ligation but are difficult to generate. The native chemical ligation concept was first developed by Dawson et al. in 1994 (*Science* 266, 776-779 (1994)), in which one protein or peptide with a C-terminal thioester and the other with a N-terminal cysteine selectively undergo thiol-thioester exchange and then S-to-N acyl transfer to form a larger protein or peptide (FIG. 2A). Given that a protein with a N-terminal cysteine can be recombinantly produced, the development of the concept made it feasible to synthesize large proteins with a functionalized N-terminus.

To expand the synthetic scope of native chemical ligation, a related technique termed expressed protein ligation in which a recombinant C-terminal intein fusion is used to generate a protein thioester was also developed for the synthesis of proteins with a functionalized C-terminus (*Proc Natl Acad Sci USA* 95, 6705-6710 (1998)). Another notable related technique is peptide hydrazide ligation that uses nitrous acid or acetyl acetone to convert a chemically stable peptide hydrazide to a peptide acyl azide or a peptide acyl pyrazole and then a peptide thioester for further native chemical ligation (FIG. 2A) (*Angew Chem Int Ed Engl* 50, 7645-7649 (2011), *Angew Chem Int Ed Engl* 57, 11634-11639 (2018)).

Although developed extensively, further technological improvement in protein ligation is still in great demand due to numerous limitations associated with existing ligation techniques. For instance, the production of a protein thioester using the intein fusion approach is not guaranteed for a lot of proteins. The stringent requirement for intein catalysis to generate a protein thioester prevents the processing of many fusion proteins that are expressed insolubly and hard to fold.

Moreover, the C-terminal residue of a targeted protein that is immediate to the intein N-terminus also significantly impacts the protein splicing efficiency, which leads to low splicing efficiency for residues such as proline at this site. The purification of an intein fusion also requires significant caution for avoiding premature hydrolysis.

A split intein may be used to prevent premature hydrolysis. However, such processes add more procedural complexity. Therefore, a need exists for a more facile method to functionalize a protein at its C-terminus for protein ligation that requires no enzymatic catalysis, can be broadly applied, and maintains high efficiency in different protein C-terminal sequence contexts. Various embodiments of the present disclosure address the aforementioned need.

In some embodiments, the present disclosure pertains to methods of conjugating a molecule to a polypeptide. In some embodiments illustrated in FIG. 1, the methods of the present disclosure include modifying one or more thiol residues of the polypeptide (step 10) and associating the polypeptide with the molecule (step 12) to result in a reaction between a nucleophilic moiety on the molecule and the one or more modified thiol residues (step 14) and the conjugation of the molecule to the polypeptide (step 16).

As set forth in more detail herein, the methods of the present disclosure can have numerous embodiments. In particular, various methods may be utilized to modify various cysteine residues of various polypeptides. Various methods may also be utilized to associate polypeptides with various molecules. Moreover, various reactions may occur between various nucleophilic moieties on molecules and modified thiol residues on polypeptides to result in the conjugation of the molecules to the polypeptides.

Polypeptides

The methods of the present disclosure can be utilized to conjugate numerous types of polypeptides to molecules. For instance, in some embodiments, the polypeptides include peptide molecules. In some embodiments, the polypeptides include proteins. In some embodiments, the proteins include recombinant proteins.

In some embodiments, the polypeptide includes, without limitation, ubiquitin (Ub), ubiquitin-like proteins (Ubls), and combinations thereof. In some embodiments, the Ub and Ubl proteins include, without limitation, SUMO1, SUMO2, SUMO3, SUMO4, ISG15, FAT10, MNSF beta, UFM1, ATG12, URM1, HUB1, GABARAP, GABARAPL2, and combinations thereof.

In some embodiments, the polypeptide includes one or more non-canonical amino acids. In some embodiments, the polypeptide includes both canonical and non-canonical amino acids. In some embodiments, the polypeptides include post-translational modifications or chemical modifications.

The one or more thiol residues to be modified can be located at numerous polypeptide regions. For instance, in some embodiments, the one or more thiol residues can be at or near the N-terminus of polypeptides, near the C-terminus of polypeptides, or within the middle regions of polypeptides. In some embodiments, the one or more thiol residues are near the C-terminus of a polypeptide but not the last amino acid at the C-terminus.

The polypeptides of the present disclosure can include different numbers of thiol residues. For instance, in some embodiments, the polypeptides of the present disclosure can include a single thiol residue. In some embodiments, the single thiol residue is located near the C-terminus of the polypeptide but not the last amino acid at the C-terminus. In some embodiments, the polypeptides of the present include more than one thiol residue. In some embodiments, the polypeptides of the present include a plurality of thiol residues.

The polypeptides of the present disclosure may include various types of thiol residues. For instance, in some embodiments, the one or more thiol residues are part of one or more cysteines on the polypeptide. In some embodiments, the one or more thiol residues are part of one or more thiol-containing non-canonical amino acids on the polypeptide.

In some embodiments, the polypeptides of the present disclosure can include fluorophores, chromophores, or other molecules directly conjugated to their C-terminus. For instance, in some embodiments, the polypeptides of the present disclosure include Ub and Ubl proteins with fluorophores, chromophores, or other molecules directly conjugated to their C-terminus.

Modification of Thiol Residues

The one or more thiol residues on the polypeptides of the present disclosure can be modified in various manners. For instance, in some embodiments, the modification occurs by cyanylation of the one or more thiol residues. In some embodiments, cyanylation includes attachment of cyano groups to sulfur atoms of the one or more thiol residues to form thiocyanato groups. In some embodiments, the thiocyanato group undergoes reversible intramolecular addition with a nearby N-amide group to generate a 1-acyl-2-iminothiazolidine intermediate. In some embodiments, the nearby N-amide group is a cysteine N-amide.

Cyano groups may be attached to sulfur atoms in various manners. For instance, in some embodiments, cyano groups may be attached to sulfur atoms by associating the polypeptides of the present disclosure with reagents that include cyano groups. In some embodiments, the reagent is 2-nitro-5-thiocyanatobenzoic acid (NTCB). In some embodiments, the reagent is a cyanide salt. In some embodiments, the cyanide salt includes, without limitation, sodium cyanide and potassium cyanide. In some embodiments, the reagent is 1-cyano-4-dimethylaminopyridinium.

Molecules

The polypeptides of the present disclosure may be associated with various types of molecules. For instance, in some embodiments, the molecules include, without limitation, small molecules, macromolecules, lipids, oligonucleotides, peptides, polypeptides, proteins, polyethylene glycols, fluorophores, chromophores, and combinations thereof.

In some embodiments, the molecules of the present disclosure include therapeutic peptides. In some embodiments, the therapeutic peptides include, without limitation, exenatide, human calcitonin, salmon calcitonin, enfuvirtide, bivalirudin, teriparatide, thymosin alpha, liraglutide, lixisenatide, dulaglutide, semaglutide, taspoglutide, pexiganan, histone H2A, RNAse H, and combinations thereof.

The molecules of the present disclosure can include various types of nucleophilic moieties. For instance, in some embodiments, the nucleophilic moieties include amine groups. In some embodiments, the amine groups include, without limitation, primary amines, secondary amines, hydrazine, hydrazides, hydroxylamines, O-alkylhydroxylamines, ammonia, and combinations thereof.

Association of Polypeptides with Molecules

Various methods may also be utilized to associate the polypeptides of the present disclosure with the molecules of the present disclosure. For instance, in some embodiments, the association occurs by mixing the polypeptides with the molecules. In some embodiments, the mixing occurs by stirring. In some embodiments, the mixing occurs by sonicating.

The association of the polypeptides and molecules of the present disclosure can occur at various times. For instance, in some embodiments, the association occurs before the one or more thiol residues of the polypeptides of the present disclosure are modified. In some embodiments, the association occurs during the modification of the one or more thiol residues of the polypeptides of the present disclosure. In some embodiments, the association occurs after the modification of the one or more thiol residues of the polypeptides of the present disclosure.

Conjugation of Molecules to Polypeptides

The molecules of the present disclosure may be conjugated to the polypeptides of the present disclosure through various mechanisms. For instance, without being bound by theory, conjugation can occur when modified thiol residues in the polypeptides of the present disclosure react with nucleophilic moieties of the molecules of the present disclosure in order to result in the removal of the modified thiol-containing amino acid residues and thereby result in the conjugation of the molecules to the polypeptides. In a more specific embodiment, nucleophilic moieties on molecules react with a 1-acyl-2-iminothiazolidine intermediate derived from modified thiols in order to replace 2-iminothiazolidine in a nucleophilic acyl substitution and thereby result in the conjugation of the molecule to the polypeptide.

Applications and Advantages

The methods of the present disclosure provide numerous advantages and applications. For instance, in some embodiments, the methods of the present disclosure can be utilized to produce numerous conjugated proteins in a facile manner. In some embodiments, the methods of the present disclosure require no enzymatic catalysis. In some embodiments, the methods of the present disclosure can be utilized to conjugate structurally constrained protein regions to molecules. In some embodiments, the methods of the present disclosure can be utilized to conjugate proteins to molecules under denatured conditions. Moreover, the methods of the present disclosure can expand to a great extent the synthetic capacity of protein chemistry.

As such, the methods of the present disclosure can have broad applications in numerous avenues of research fields and industrial processing of proteins and peptides. For instance, in some embodiments, the methods of the present disclosure can be used to generate many protein-based reagents, such as ubiquitin and ubiquitin-like proteins with C-terminal modifications. In some embodiments, the methods of the present disclosure can be used to synthesize many commercial therapeutic peptides that have a C-terminal amide, such as exenatide, human calcitonic, salmon calcitonin, eufuvirtide, bivalirudin, teriparatide, thymosin alpha, liraglutide, lixisenatide, dulaglutide, semaglutide, taspoglutide, histone H2A, RNAse H, pexiganan, and combinations thereof.

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Activated Cysteine-Directed Protein Ligation

In this Example, Applicants utilized a small molecule to cyanylate a cysteine in a recombinant protein. The experimental results demonstrate that cysteine's N-side amide bond was directly activated in mild aqueous conditions to undergo nucleophilic acyl substitution with a number of amines including hydrazine that can be used for further protein ligation. Applicants demonstrated the versatility of this activated cysteine-directed protein ligation technique with the successful synthesis of ubiquitin conjugates, ubiquitin-like protein conjugates, histone H2A with a posttranslational modification, RNAse H that actively hydrolyzed RNA, and exenatide that is a commercial therapeutic peptide.

Figure 2B:
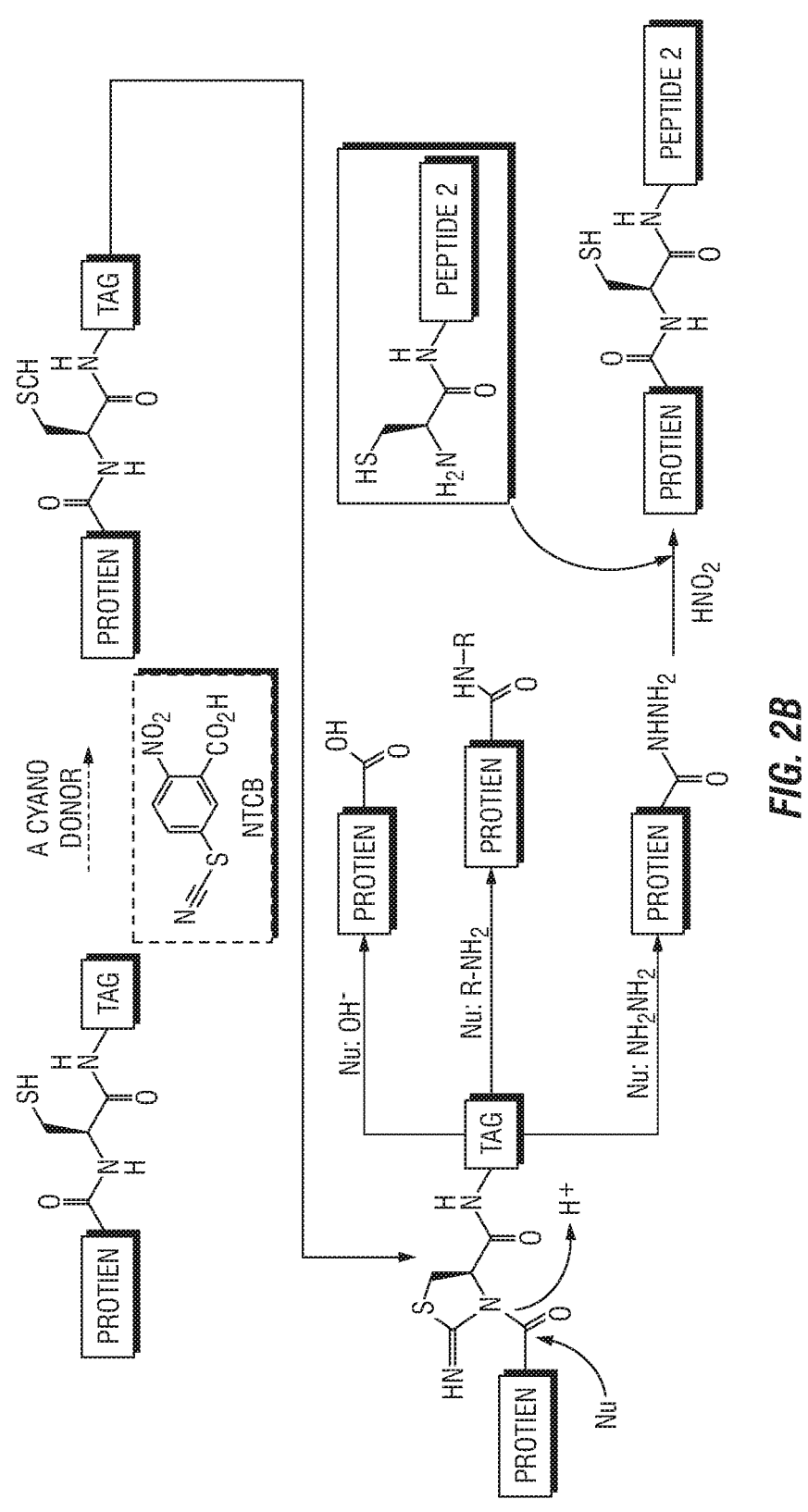
FIG. 2B illustrates a proposed protein ligation technique based on nucleophilic acyl substitution of an activated cysteine residue in a recombinant protein with a nucleophilic amine. Without a nucleophilic amine, the protein undergoes hydrolysis. When the nucleophile is hydrazine, the afforded protein hydrazide can then undergo peptide hydrazide ligation to form a larger protein.

Applicants developed the method in this Example based on an industrial chemical process known as leather tanning by cyanides. Cyanide salts that reduce disulfide bonds in proteins were used in the early 20$^{th}$ century to treat animal hides and wools. During the process, a cyanide covalently attaches to a protein cysteine to form a thiocyanato group that undergoes reversible intramolecular addition with the cysteine N-amide to generate a 1-acyl-2-iminothiazolidine intermediate. The amide bond in this intermediate is significantly weakened in comparison to a regular protein amide and therefore slowly hydrolyzes to split the protein (FIG. 2B).

The aforementioned reaction was utilized to map protein sequences and replace cyanide salts with other cyanylating reagents such as 2-nitro-5-thiocyanatobenzoic acid (NTCB) that transfers the cyano group directly to a reduced protein cysteine for avoiding the formation of highly toxic cyanide wastes. Applicants reasoned that a strongly nucleophilic amine provided in the reaction mixture might undergo nucleophilic acyl substitution with the 1-acyl-2-iminothiazolidine intermediate to replace 2-iminothiazolidine and therefore the hydrolysis process might be effectively curbed and a new protein ligation technique might be developed.

Applicants named the aforementioned novel technique as activated cysteine-directed protein ligation. Since this ligation is chemically based, Applicants expected it to be highly controllable, selective, and versatile such as functioning for proteins both soluble and insoluble and undertaking in both native and denatured conditions. To demonstrate the feasibility of this new ligation, Applicants synthesized Ac-Xxx-Cys-NH$_2$ dipeptides in which the Xxx identity varied between seven native amino acids including proline and carried out their reactions with equivalent amounts of NTCB and then ligation with propargylamine in a 1:1 DMF/H$_2$O solvent. Applicants' results showed that all dipeptides reacted with propargylamine to form desired products with varied yields (Table 1).

TABLE 1

| Yields of dipeptide ligation with propargylamine. | | | | |
|---|---|---|---|---|
| Peptide | Amount (g) | Ligation products | Amount (g) | Yield (%) |
| Gly-Cys-OMe | 0.6 | Gly-Pa | 0.12 | 56.6 |
| Ala-Cys-OMe | 0.6 | Ala-Pa | 0.11 | 48.6 |
| Leu-Cys-OMe | 2.0 | Leu-Pa | 0.7 | 87.5 |
| Phe-Cys-OMe | 1.8 | Phe-Pa | 0.65 | 88.3 |
| Trp-Cys-OMe | 2.5 | Trp-Pa | 0.8 | 78.4 |
| Asp-Cys-OMe | 0.9 | Asp-Pa | 0.05 | 13.8 |
| Pro-Cys-OMe | 2.0 | Pro-Pa | 0.16 | 25.4 |

Encouraged by Applicants' small molecule results, Applicants went on to test this new ligation technique with recombinant proteins. Ubiquitin (Ub) is natively devoid of cysteine.

Applicants chose Ub as a model protein for demonstration. Applicants produced recombinant native Ub and Ub with both a G76C mutation and a C-terminal 6×His tag (Ub-G76C-6H) in E. coli and purified them to homogeneity. Applicants then ligated Ub-G76C-6H with a number of amine-containing molecules, including both L- and D-amino acids (FIG. 3A) by adding 5 mM NTCB and a 50-1000 mM amine simultaneously to a 2 mg/mL Ub-G76C-6H solution at pH 9 for an overnight incubation at 37° C.

Applicants selected seven L-amino acids for reactions to represent amino acids in different chemical categories and also different sizes. For all tested compounds including proline that has a secondary amine and two D-amino acids, Applicants obtained ligation products with high yields. After using Ni$^{2+}$ charged resins to simply remove unreacted intermediates, Applicants analyzed all twelve ligation products and the two original Ub and Ub-G76C-6H proteins by electrospray ionization mass spectrometry (ESI-MS) analysis. For all analyzed proteins, their deconvoluted ESI-MS spectra displayed clearly observable monoisotopic peaks.

Since there is no commercial software for calculating protein monoisotopic peaks, Applicants wrote a Python script to calculate all theoretical monoisotopic masses and their relative intensities for all proteins and compared them to the determined ESI-MS spectra. Applicants' results showed that determined monoisotopic masses for all proteins agreed very well with their theoretic values in terms of both molecular weight and intensity. Hydrolysis products were either non-detectable or at very low levels. To simplify the comparison, Applicants wrote another Python script to integrate deconvoluted monoisotopic peaks and then calculate the average molecular weights and intensities for all detected protein species in a particular spectrum. The final results are presented in FIGS. 3B and 3C.

For all determined average molecular weights, the peaks matched their theoretical values with a deviation of ±0.3 Da. For all twelve ligation products, Applicants detected very few minor peaks in their ESI-MS spectra indicating that all reactions were very selective. One ligation product Ub-G76G is native Ub itself. Its ESI-MS spectrum in FIG. 3C matched that of recombinantly expressed native Ub in FIG. 3B. So far, Applicants' data demonstrated that activated cysteine-directed protein ligation on a recombinant protein works exactly according to what Applicants proposed and this reaction is effective for amines that are primary, secondary, hydrazine, and amino acids with different configurations, characteristics, and sizes.

The ligation with hydrazine was done in both native and denatured conditions. The results from two conditions showed minimal differences. Ubiquitin natively has a G75 residue that has the lowest steric hindrance among all amino acids. In Ub-G76C-6H, the glycine immediately N-terminal to G76C might have permitted easy processing of the ligation. Other residues that have different chemical properties and/or are sterically hindered might impede the ligation. To resolve this concern, Applicants mutated G75 in Ub-G76C-6H to six other residues that are large in size, charged, and/or having a secondary amine, recombinantly expressed them, analyzed them with ESI-MS (FIG. 3D), and then reacted them in a one-pot fashion with NTCB and hydrazine.

Applicants chose hydrazine in their demonstration since its ligation products are protein hydrazides that can be coupled further with peptide hydrazide ligation for making even larger proteins. All reactions progressed well and their reaction products displayed average molecular weights matching well to their theoretic values (FIG. 3E), demonstrating that the residue immediately N-terminal to the targeted cysteine has little detrimental effect on the ligation process.

Putting a cysteine residue right after Ub G76 led to similar ligation results with hydrazine (FIGS. 3D and 3E) and with allylamine, propargylamine, and glycine. Ub has a flexible C-terminus that may facilitate the ligation. To show that the ligation may work in a more structurally constrained environment, Applicants introduced a cysteine mutation at K48 and K63, two residues in the globular region of Ub and used the two afforded Ub mutants to undergo activated cysteine-directed protein ligation with hydrazine. ESI-MS of reaction mixtures showed successful formation of two desired protein hydrazides indicating that the ligation works well in a structurally constrained protein region. Ligation both in a structurally constrained protein region and under a denatured condition is something that the traditional intein method cannot perform well. Collectively, Applicants' data strongly demonstrates the versatility of the activated cysteine-directed protein ligation technique.

In eukaryotic cells, Ub and Ub-like proteins (Ubls) can be posttranslationally attached to proteins for their functional regulation. It has been shown that replacing the C-terminal glycine in Ub, SUMO1-3, NEED8, and ISG15 with propargylamine using either the intein based approach or total synthesis afforded optimal probes to bind covalently to cysteine proteases that catalytically remove Ub or Ubls from their conjugated proteins in cells.

To recapitulate these results and demonstrate the broad application scope of Applicants' activated cysteine-directed protein ligation, Applicants recombinantly expressed Ub, SUMO1-4, NEDD8, ISG15, GABARAP, GABARAPL2, UFM1, URM1, and MNSFβ (FLAG-Ub/Ubl-GxC-6H: x denotes the terminal glycine position) that all contained a C-terminal Gly-to-Cys mutation and were also fused with a N-terminal FLAG tag and a C-terminal 6×His tag, purified them to homogeneity, and then carried out their ligation with propargylamine in the presence of NTCB.

Figure 4A:
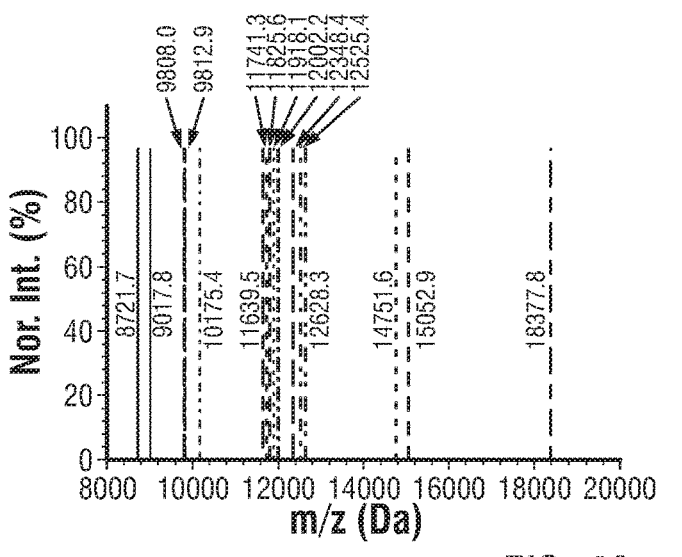
FIG. 4A shows a deconvoluted and integrated ESI-MS of Ub and Ubls conjugated to Pa or AMC. Ub-AMC was synthesized from Ub-G76C-6H. All other Pa- and AMC-conjugated Ub and Ubls were generated from FLAG-tagged proteins. Ub and Ubls with their C-terminal glycine mutated to cysteine were expressed and purified as a protein fused with a N-terminal FLAG tag and a C-terminal 6×His tag. ISG15, SUMO1-4, and MNSFβ have a native cysteine residue. This cysteine was mutated to alanine or serine in all six expressed proteins for avoiding side reactions. The label "" indicates this mutation. All detected molecular weights agreed well with their theoretic values with a deviation range of ±0.5 Da.
Figure 4B:
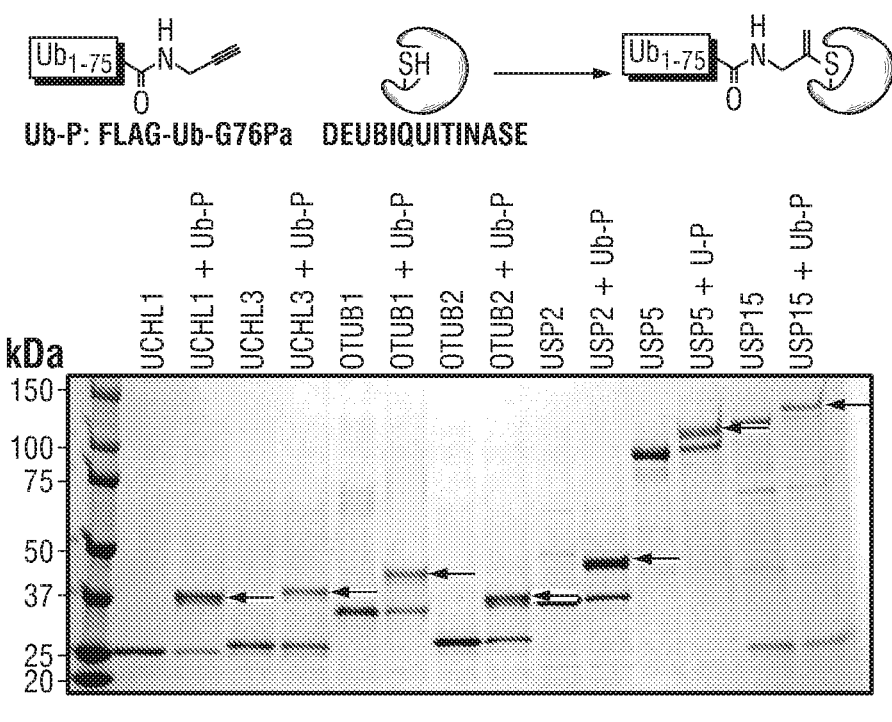
FIG. 4B shows the formation of covalent adducts between FLAG-Ub-G76 Pa and a number of deubiquitinases. Red arrows point to the generated adducts.

ISG15, SUMO1-4, and MNSFβ natively contain a cysteine residue. This cysteine was mutated to alanine or serine to avoid non-targeted ligation at its location. SDS-PAGE analysis indicated high ligation yields. ESI-MS analysis of all 12 products indicated their successful and efficient synthesis (FIG. 4A). In comparison to both intein based and total synthesis approach, Applicants' method for the synthesis of these propargylamine conjugates is much simpler and easier to control. To reproduce literature results, Applicants then used synthesized Ub-propargylamine conjugate, FLAG-Ub-G76 Pa, to react with seven known cysteine deubiquitinases and observed efficient covalent adduct formation for all tested enzymes by both SDS-PAGE analysis and Western blotting (FIG. 4B).

Figure 4C:
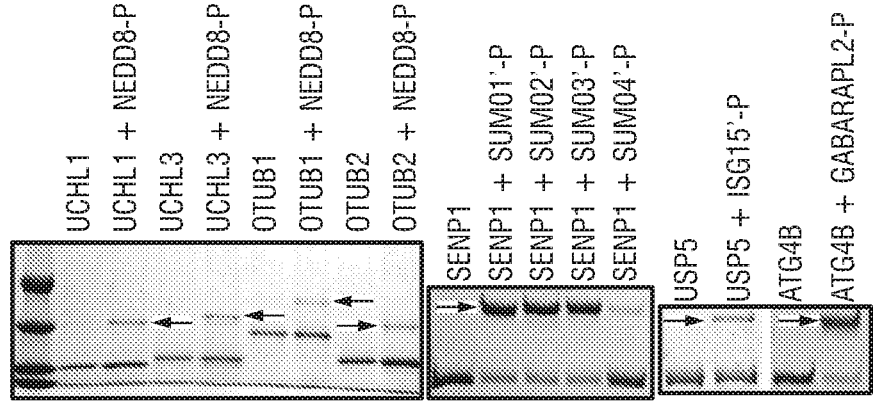
FIG. 4C shows the formation of covalent adducts, indicated by red arrows, between different FLAG-Ubl-Pa conjugates and Ubl proteases.

Applicants also performed similar tests for 7 Ubl-propargylamine conjugates and observed their covalent binding to a number of cysteine proteases as shown in FIG. 4C. Some cysteine proteases such as SENP1 have only been vaguely confirmed in previous work to deconjugate corresponding Ubls such as SUMO4 shown in the gel. Given that all synthesized FLAG-Ub/Ubl-propargylamine conjugates, of which five are synthesized for the first time, can be used as activity-based probes to profile the proteome of Ub and Ubl proteases in different tissues and cells, Applicants' method that readily makes these probes available and can be performed in almost any biology lab will, in no doubt, promote their adoption for advancing Ub and Ubl biology studies. Ub and Ubls conjugated directly to 7-amino-4-methylcoumarin (AMC) at their C-terminus are useful fluorogenic substrates of Ub and Ubl proteases.

Figures 3A, 3B, 3C:
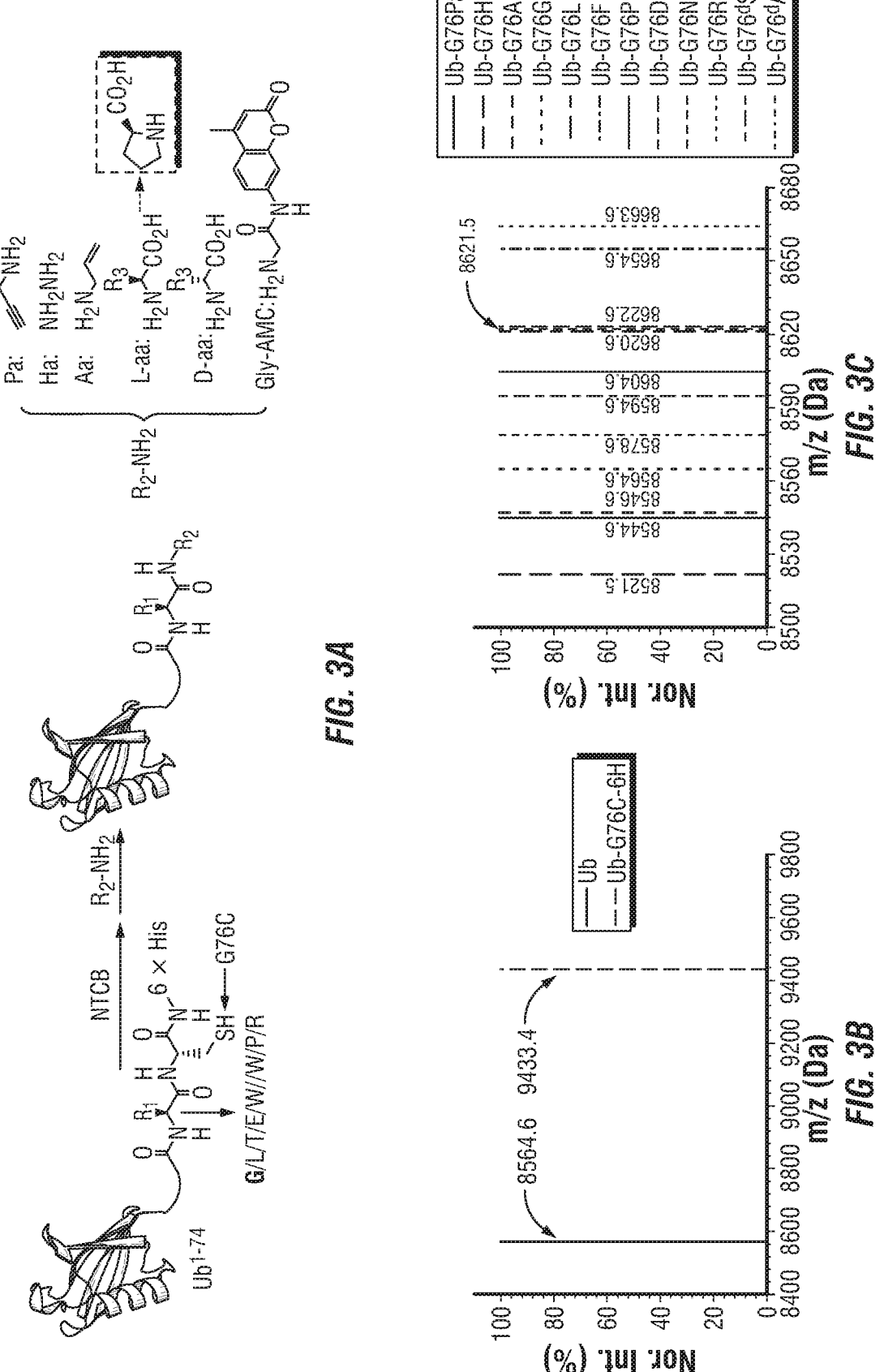
FIG. 3A illustrates a schematic diagram to show the activation of recombinant Ub proteins containing a cysteine by 2-nitro-5-thiocyanatobenzoic acid (NTCB) followed by nucleophilic acyl substitution with amines, both primary and secondary, to generate different Ub conjugates. The native Ub has 76 residues and glycine at the $75^{th}$ and $76^{th}$ positions.
FIG. 3B shows the deconvoluted and integrated ESI-MS of wild type Ub and Ub-G76C-6H. 6H represents a 6×His tag.
FIG. 3C shows the deconvoluted and integrated ESI-MS of Ub conjugates that were converted from Ub-G76C-6H and had different ligated molecules at the G76 position. Pa, Ha, and Aa are three small molecule amines shown in FIG. 3A. All other ligated molecules are amino acids whose one letter codes are used for labeling. All amino acids are in the L-configuration except two D-amino acids with a footnote.
Figure 3D:
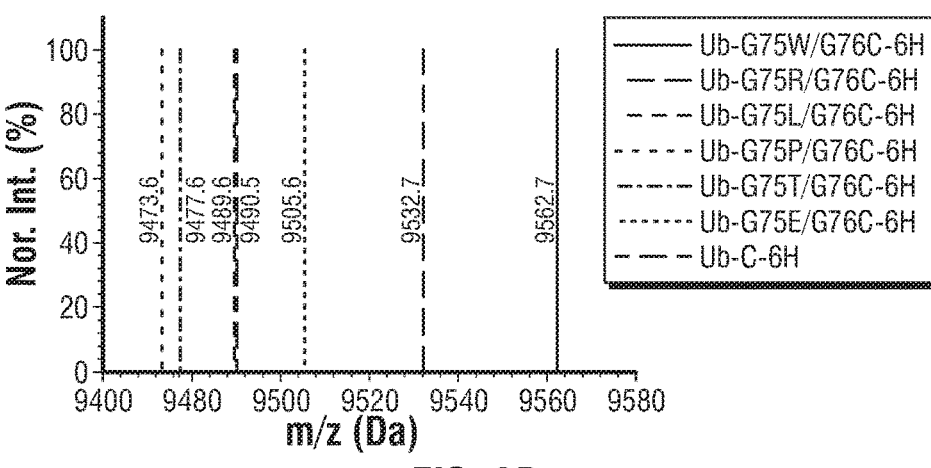
FIGS. 3D and 3E show the deconvoluted and integrated ESI-MS of 7 recombinant Ub proteins and products of their reactions with NTCB and Ha. C in Ub-C-6H represents cysteine. All detected molecular weights agreed well with theoretic values in a deviation range of ±0.3 Da.
Figure 3E:
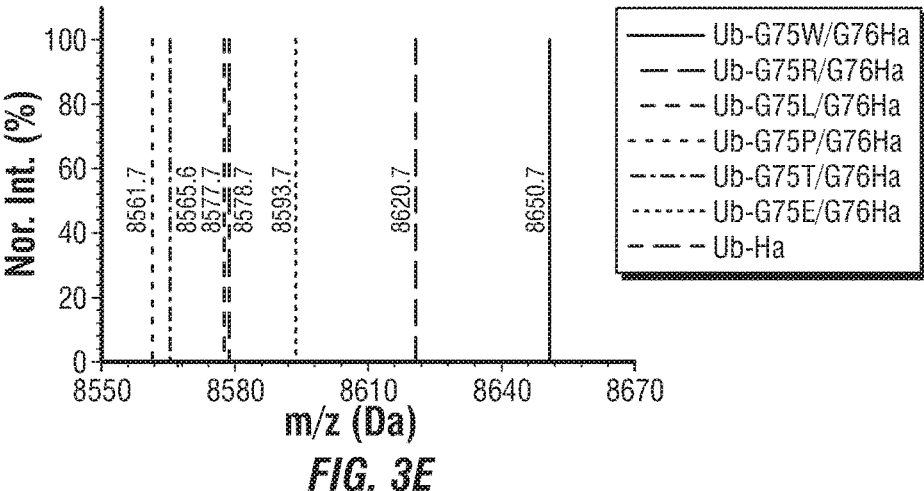
Figures 4D, 5A:
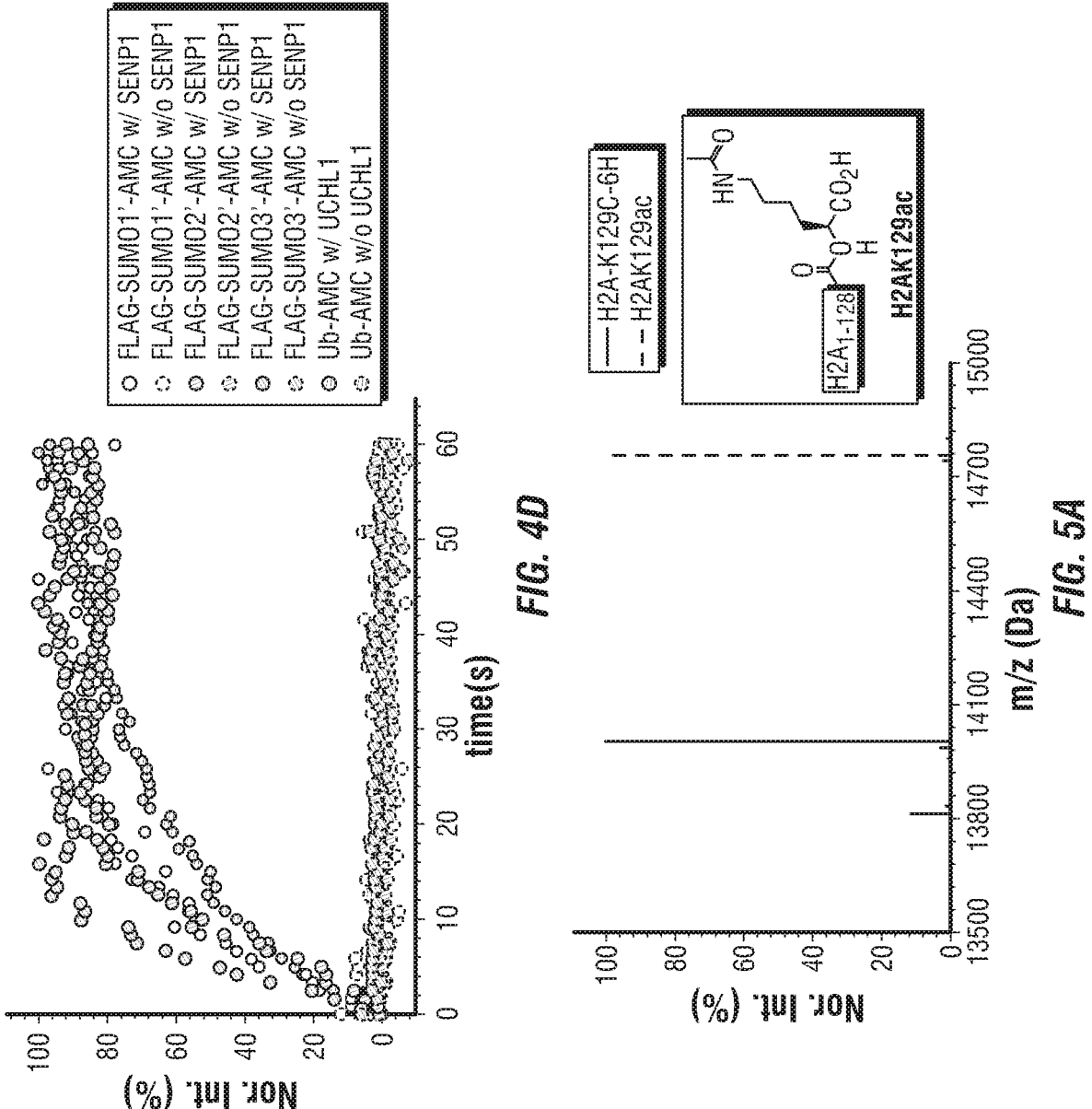
FIG. 4D shows the Ub or Ubl protease-catalyzed AMC release from Ub-AMC and three FLAG-SUMO-AMC conjugates.
FIG. 5A shows the deconvoluted and integrated ESI-MS of H2A-K129C-6H and H2AK129ac. H2A-K129C-6H was recombinantly expressed and then reacted with NTCB and $N^\epsilon$-acetyl-lysine to afford H2AK129ac.

Applicants have demonstrated the synthesis of four Ub/Ubl-AMC conjugates, Ub-AMC and FLAG-SUMO1-3-AMC by Applicants' activated cysteine-directed protein ligation of their corresponding recombinantly produced Ub-G76C-6H and FLAG-SUMO1-3-GxC-6H proteins to Gly-AMC (FIG. 3A). Applicants' ESI-MS analysis of all four products confirmed their successful synthesis (FIG. 4A) and the following activity assays showed that they served as active substrates for cysteine proteases UCHL1 and SENP1, respectively (FIG. 4D). Overall, Applicants' combined data of Ub and Ubl related synthesis establish the broad scope of the activated cysteine-directed protein ligation technique.

Histone H2A can undergo posttranslational acetylation at its terminal lysine, K129. The functional investigation of this acetylation such as how it influences the structure and dynamics of the nucleosome will require the synthesis of the corresponding acetyl-histone, H2AK129ac. Applicants chose to synthesize H2AK129ac to demonstrate that their method can be applied to the synthesis of histones with C-terminal modifications. Applicants first recombinantly produced H2A-K129C-6H, a H2A protein with a K129C mutation and a C-terminal 6×His tag and then ligated it to N$^\varepsilon$-acetyl-lysine with the assistance of NTCB.

Figure 5B:
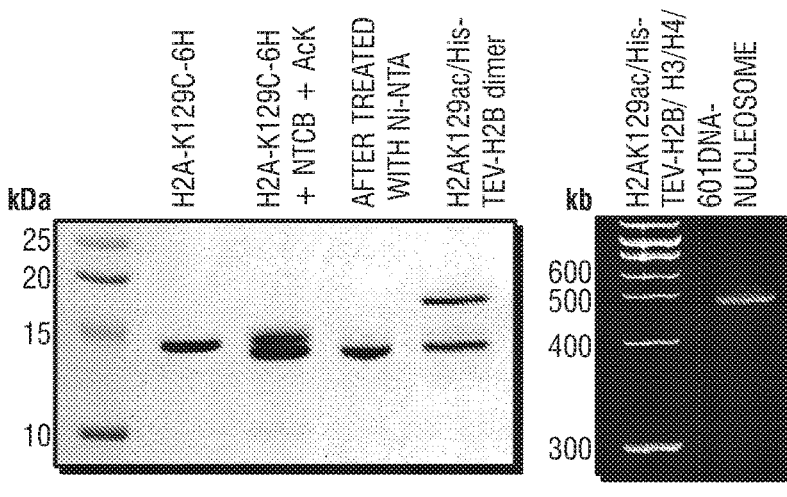
FIG. 5B illustrates the synthesis of H2AK129ac, its isolation, and folding into an H2AK129ac/H2B dimer and then a nucleosome. The purification of H2AK129ac was achieved by extracting the unreacted intermediate using Ni-NTA resins.

The ESI-MS spectrum of the reaction product showed the formation of H2AK129ac (FIG. 5A). Applicants folded successfully H2AK129ac into a dimer with H2B and subsequently into a nucleosome (FIG. 5B), making it possible to study effects of H2AK129ac on the nucleosome structure and functions.

For all ligation reactions that Applicants performed thus far in this Example, they involved small molecules with only one amino group for avoiding side product formation. For ligation with larger molecules that have more than one amino group, one can couple Applicants' ligation method with peptide hydrazide ligation to resolve nonspecificity issues.

Figure 5C:
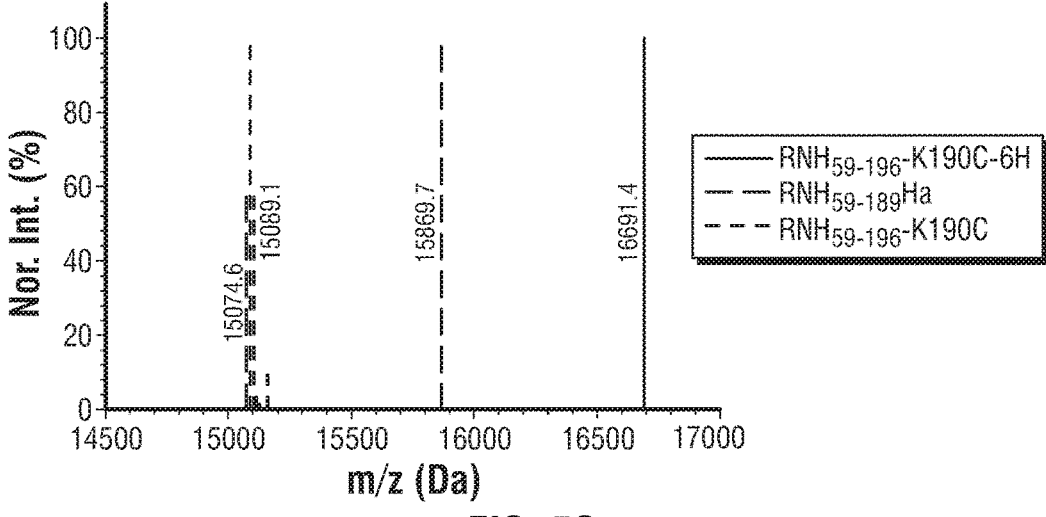
FIG. 5C shows the deconvoluted and integrated ESI-MS of $RNH_{59\text{-}196}$-K190C-6H, $RNH_{59\text{-}189}$-Ha, and $RNH_{59\text{-}196}$-K190C. $RNH_{59\text{-}196}$-K190C-6H was recombinantly expressed in *E. coli*. It was reacted with NTCB and hydrazine to afford $RNH_{59\text{-}189}$-Ha that then underwent peptide hydrazide ligation with a 7-mer $NH_2$-CADYGRK-OH peptide (SEQ ID NO:1) to form a catalytic active $RNH_{59\text{-}196}$-K190C.
Figure 5D:
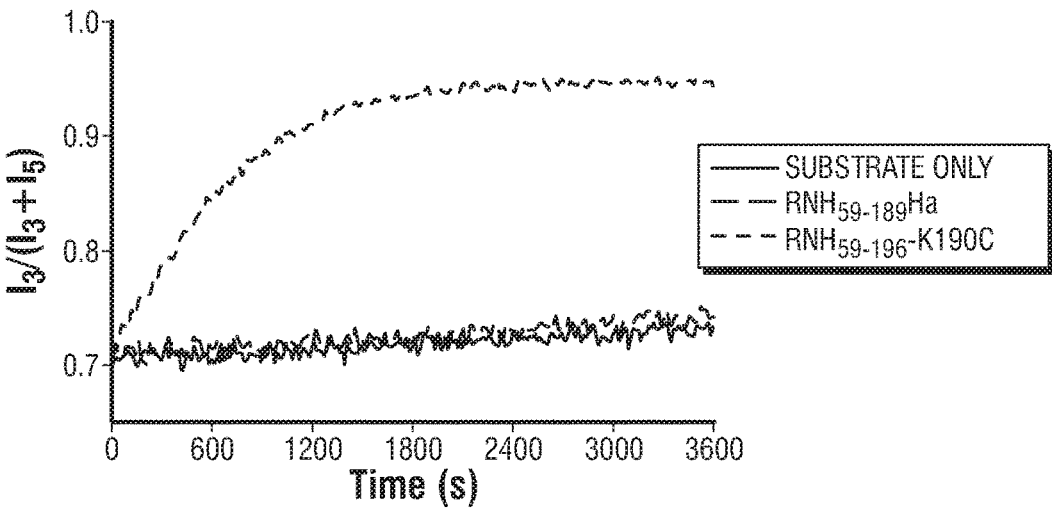
FIG. 5D shows the catalytic hydrolysis of a RNA substrate by $RNH_{59\text{-}196}$-K190C. The RNA substrate had a sequence 5'-Cy3-GACACCUGAUUC-Cy5-3' (SEQ ID NO: 2). A DNA fragment 5'-GAATCAGGTGTC-3' (SEQ ID NO:3) was used to form a double strand with the RNA substrate for binding to $RNH_{59\text{-}196}$-K190C. The hydrolysis led to improved Cy3 ($I_3$) and decrease Cy5 ($I_5$) emission.

To demonstrate this prospect, Applicants recombinantly produced a *B. halodurans* RNase H region with a C-terminal Cys-6×His tag ($RNH_{59-196}$-K190C-6H). Its ligation with hydrazine in the presence of NTCB led to the synthesis of $RNH_{59-189}$-Ha, a protein hydrazide that Applicants processed further to undergo peptide hydrazide ligation with a 7-mer peptide, $NH_2$-CADYGRK-OH (SEQ ID NO:1) to afford a ligated product $RNH_{59-196}$-K190C. ESI-MS analysis showed the successful synthesis of both $RNH_{59-189}$-Ha and $RNH_{59-196}$-K190C (FIG. 5C). Similar to what has been found in previous peptide hydrazide ligation reactions, Applicants also detected a minor hydrolysis product at 15074.6 Da. The ligated product $RNH_{59-196}$-K190C was catalytically active to hydrolyze an RNA substrate as shown in FIG. 5D. However, $RNH_{59-189}$-Ha was completely inactive toward this substrate. Applicants' data related to the synthesis of RNase H demonstrated that the activated cysteine-directed protein ligation can couple to peptide hydrazide ligation for ligation with large peptides or even protein fragments.

In summary, Applicants have developed an activated cysteine-directed protein ligation technique that uses a cyanylating reagent to directly activate a cysteine in a recombinant protein for ligation with amine-containing small molecules and large peptide or protein fragments when coupling with peptide hydrazide ligation. The technique requires no enzymatic catalysis and is controllable, versatile, specific, and very simple to process. It can be broadly applied to synthesize a large variety of proteins with unique functionalities for advanced applications in both basic and applied research. One potential industrial application of the technique is to synthesize therapeutic peptides.

Applicants have shown that the technique can be used to efficiently synthesize exenatide, a 39-mer anti-diabetic peptide that has a C-terminal amide and is therefore hard to generate using the recombinant expression approach. By expressing a 6×His-SUMO-exenatide-S39C-SA-Strep fusion that can be largely produced in *E. coli* followed by the treatment with SUMO protease and then processing it by activated cysteine-directed ligation with L-serinamide, Applicants showed that exenatide can be easily procured.

Similar applications to synthesize other therapeutic peptides or proteins are anticipated. Applicants' ligation technique requires the activation of cysteine, one of the two lowest occurring amino acids in proteins. Non-targeted cysteines need to be mutated. For proteins with essential cysteines, one possible solution for using Applicants' technique is to couple it with the noncanonical amino acid mutagenesis technique. Photocaged cysteines have been genetically incorporated into proteins by amber suppression. The incorporation of a photocaged cysteine to essential cysteine sites in a protein followed by activated cysteine-directed protein ligation and then decaging to release protected essential cysteines will allow the processing of proteins with non-targeted cysteines.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of conjugating a molecule to a polypeptide, said method comprising:

modifying one or more thiol residues on the polypeptide, wherein the modifying comprises cyanylation of the one or more thiol residues, and wherein the one or more thiol residues are part of one or more thiol-containing non-canonical amino acids on the polypeptide; and associating the polypeptide with the molecule, wherein the associating results in the conjugation of the molecule to the polypeptide through a reaction between a nucleophilic moiety on the molecule and the one or more modified thiol residues.

2. The method of claim 1, wherein the cyanylation comprises attachment of cyano groups to sulfur atoms of the one or more thiol residues to form thiocyanato groups, and wherein the thiocyanato groups undergo reversible intramolecular addition with a nearby N-amide group to generate a 1-acyl-2-iminothiazolidine intermediate.

3. The method of claim 2, wherein the nearby N-amide group is a cysteine N-amide.

4. The method of claim 2, wherein the attachment comprises associating the polypeptide with a reagent comprising the cyano groups.

5. The method of claim 4, wherein the reagent is 2-nitro-5-thiocyanatobenzoic acid (NTCB).

6. The method of claim 2, wherein the nucleophilic moiety on the molecule reacts with the 1-acyl-2-iminothiazolidine intermediate to replace 2-iminothiazolidine in a nucleophilic acyl substitution reaction and result in the conjugation of the molecule to the polypeptide.

7. The method of claim 1, wherein the associating comprises mixing the polypeptide with the molecule.

8. The method of claim 1, wherein the associating occurs at a time selected from the group consisting of before, during, and after the modifying step.

9. The method of claim 1, wherein the polypeptide comprises at least one of a peptide or a protein.

10. The method of claim 1, wherein the one or more thiol residues are located at the C-terminus of the polypeptide but not the last amino acid at the C-terminus.

11. The method of claim 1, wherein the polypeptide comprises one or more non-canonical amino acids.

12. The method of claim 1, wherein the one or more thiol residues are part of one or more cysteines on the polypeptide.

13. The method of claim 1, wherein the molecule is selected from the group consisting of small molecules, macromolecules, lipids, oligonucleotides, peptides, polypeptides, proteins, polyethylene glycols, fluorophores, chromophores, and combinations thereof.

14. The method of claim 1, wherein the molecule comprises a peptide.

15. The method of claim 1, wherein the nucleophilic moiety is an amine group.

16. The method of claim 15, wherein the amine group is selected from the group consisting of hydrazine, primary amines, secondary amines, hydrazine, hydrazides, hydroxylamines, O-alkylhydroxylamines, ammonia, and combinations thereof.

17. The method of claim 1, wherein the method does not require enzymatic catalysis.

18. The method of claim 1, wherein the polypeptide is selected from the group consisting of ubiquitin (Ub), ubiquitin-like proteins (Ubls), SUMO1, SUMO2, SUMO3, SUMO4, ISG15, FAT10, MNSF beta, UFM1, ATG12, URM1, HUB1, GABARAP, GABARAPL2, and combinations thereof.

19. The method of claim 1, wherein the molecule is a therapeutic peptide selected from the group consisting of exenatide, human calcitonin, salmon calcitonin, enfuvirtide, bivalirudin, teriparatide, thymosin alpha, liraglutide, lixisenatide, dulaglutide, semaglutide, taspoglutide, pexiganan, histone H2A, RNAse H, and combinations thereof.

*    *    *    *    *

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Cys Ala Asp Tyr Gly Arg Lys
1               5

<210> SEQ ID NO 2
<211> LENGTH: 12
<212> TYPE: RNA
<213> ORGANISM: Artificial Sequence
<220> FEATURE:
<223> OTHER INFORMATION: Synthetic Construct

<400> SEQUENCE: 2
gacaccugau uc                                                    12

<210> SEQ ID NO 3
<211> LENGTH: 12
<212> TYPE: DNA
<213> ORGANISM: Artificial Sequence
```

-continued

```
<220> FEATURE:
<223> OTHER INFORMATION: Synthetic Construct

<400> SEQUENCE: 3
gaatcaggtg tc                                                                    12
```